United States Patent [19]

Ayusawa et al.

[11] Patent Number: 4,544,749
[45] Date of Patent: Oct. 1, 1985

[54] PROCESS FOR PRODUCTION OF PIPERIDINE

[75] Inventors: Tadashi Ayusawa; Tadamichi Aoki; Ryozo Hamana, all of Ami, Japan

[73] Assignee: Mitsubishi Petrochemical Company Limited, Tokyo, Japan

[21] Appl. No.: 583,237

[22] Filed: Feb. 24, 1984

[30] Foreign Application Priority Data

Mar. 2, 1983 [JP] Japan ............................... 58-34012

[51] Int. Cl.$^4$ ............................................ C07D 295/02
[52] U.S. Cl. ................................... 546/184; 549/492
[58] Field of Search ........................................ 546/184

[56] References Cited

U.S. PATENT DOCUMENTS 2,166,183  7/1939  Signaigo ............................... 564/492

OTHER PUBLICATIONS

Wilson, C., *J. Am. Chem. Soc.,* 67, 693, (1945).
*Chemical Abstracts,* 90:87158m, (1979), [Sokolskii, D. et al., *Khim. Prom-St.,* 1978, (12), 901–3].
*Chemical Abstracts,* 91:56726m, (1979), [Erzhanova, M. et al., *Teor. Osn. Pererab. Miner. Org. Syrya,* 1976, 3, 153–8].

*Primary Examiner*—Richard A. Schwartz
*Attorney, Agent, or Firm*—Oblon, Fisher, Spivak, McClelland & Maier

[57] ABSTRACT

Catalytic hydrogenation of furfurylamine or tetrahydrofurfurylamine in the presence of a cobalt-based catalyst into piperidine can be industrially carried out in an organic solvent, wherein addition of ammonia is not needed. It has been believed heretofore that the presence of ammonia in the hydrogenation is essential in such catalytic hydrogenation.

12 Claims, No Drawings

PROCESS FOR PRODUCTION OF PIPERIDINE

BACKGROUND OF THE INVENTION

1. Field of the Art

The present invention relates to a process for producing piperidine by liquid-phase catalytic hydrogenation of furfurylamine (FAM) and/or tetrahydrofurfurylamine (4H FAM). More specifically, the present invention relates to a process for preparing piperidine, characterized by the type of the catalyst used and by the manner in which the hydrogenation is carried out.

Piperidine is a useful compound as a starting material for pharmaceuticals, agricultural chemicals, rubber chemicals, and many other chemicals.

2. Prior Art

Hydrogenation of pyridine has been well known as a process for producing piperidine. However, a number of processes using materials other than pyridine have been proposed since pyridine is relatively expensive. Such processes comprise, for example, deammoniation-cyclization of 1,5-pentanediamine, ammonolysis of tetrahydropyran, 1,5-pentanediol or tetrahydrofurfuryl alcohol, and hydrogenation of FAM or 4H FAM. None of these processes can be made industrially practical because some starting materials used therein are not readily available or because some of these processes require high temperature reactions, result in a low yield, or are uneconomically complicated.

Among these processes, the process comprising hydrogenation of FAM or 4H FAM is expected to be an excellent industrial process if the hydrogenation can be conducted in a high yield because FAM can be produced in a high yield through reductive amination of furfural mass-produced from agricultural products, and also 4H FAM can be derived in a high yield through hydrogenation of the FAM.

It is reported in U.S. Pat. No. 2,265,201 that "a good yield of piperidine is obtained" (although no data is set forth) by adding to FAM liquid ammonia and a cobalt catalyst in an amount of 1/10 by weight of the raw material and subjecting the system to a batchwise hydrogenation reaction at 250° C. under a pressure of 200 atm. for 10 hours. It is also reported that from 4H FAM "a good yield of piperidine is obtained" in a similar manner as in the case of FAM except that carbon monoxide is further added to the system. Furthermore, it is reported that a good yield of piperidine is produced under the conditions of a high temperature and a high pressure in the presence of ammonia over a copper chromite catalyst or a nickel catalyst. It is further reported that platinum catalyst may be used, and that the use of an inert solvent such as methanol or cyclohexane is advantageous in a liquid phase reaction, although the use of both of these catalysts is not supported by working examples.

Moreover, there are reported an example wherein piperidine is obtained in a yield of 9% from FAM without addition of ammonia by using Raney nickel as a catalyst and carrying out a reaction under a pressure of 100 atm. or higher [J. Am. Chem. Soc. Vol. 67, 693 (1945)], and an example wherein piperidine is obtained in a yield of 11% by using copper chromite catalyst [Acta. Chem. Scand. Vol. 20, 591 (1966)].

As described above, the prior art requires reaction conditions which are difficult to employ in commercial operation or results in a very low yield of the desired product. Thus, it can be said as far as we are aware that the prior process for catalytic hydrogenation of FAM and/or 4H FAM is still short of the level of industrial operations.

SUMMARY OF THE INVENTION

An object of the present invention is to solve the above mentioned problems, which object can be achieved by using a specific catalyst and adopting a specific mode of hydrogenation.

The process for preparing piperidine according to the present invention comprises liquid phase catalytic hydrogenation of a starting amine selected from the group consisting of furfurylamine and tetrahydrofurfurylamine, which process is characterized in that the catalyst used therein is a cobalt-based catalyst and the starting amine is in a state of dilution with an organic solvent.

By using a cobalt-based catalyst and by conducting the catalytic hydrogenation of the amine in a state of dilution with an organic solvent, piperidine can be obtained in a high yield under moderate conditions (especially, at 250° C. or lower temperature and under 100 atm. or lower pressure) although ammonia is not added to the reaction system.

That piperidine can be obtained in a high yield under moderate conditions by using an organic solvent in place of ammonia according to the present invention, can be said to be a totally unexpected fact since the above described prior art using a cobalt catalyst requires the presence of ammonia and, moreover, the presence of ammonia is considered in the art to be essential from the viewpoint of reaction mechanisms of preventing the starting amine from deammoniation.

DETAILED DESCRIPTION OF THE INVENTION

Analysis of the Present Hydrogenation Reaction

In the present hydrogenation reaction, the oxygen-carbon bond of the furan ring is cleaved in the first place by the hydrogenation of FAM or 4H FAM to open the ring, and then piperidine which is a nitrogen-containing 6-membered ring is formed by intramolecular dehydration. Both the starting material and the product are highly reactive with respect to undesirable reactions such as polymerization. Also, the cleavage of the bond between the carbon atom at the 5-position of the furan ring and the oxygen atom may probably produce 2,5-dipropylpiperazine and n-amylamine whereby no production of piperidine is expected. Moreover, in the hydrogenation reaction, it is liable to cause cleavage of the carbon-nitrogen bond of the piperidine thus produced, resulting in undesirable reactions such as ring-opening polymerization and formation of n-amylamine. Particularly, a reaction system which does not produce n-amylamine as by-product is desired since the boiling point thereof differs from that of piperidine by only 2° C. and, thus, complicated treatment is required for the separation of these products.

In order to accelerate only the main reactions leading to piperidine while controlling these side-reactions, it is necessary to effectively combine the types of the catalyst and other factors such as solvent, pressure, temperature, and reaction time. Particularly, the combination of the catalyst with the solvent plays a fundamentally important role.

We have conducted a reaction using Raney cobalt catalyst similarly as in Example 2 of the above mentioned U.S. Pat. No. 2,265,201 except that a pressure of 135 atm. was employed, as shown in Comparative Example 1 set forth hereinafter. As a result, the yield of piperidine was as low as 22%, and most of the products were high-boiling substances, although the conversion of FAM was 99.9%. Next, we conducted a reaction similarly as described above except that methanol was added to the system, as shown in Comparative Example 2 presented hereinafter, since it is stated in the U.S. patent that methanol is useful as a solvent. However, the yield of piperidine was lower than the above mentioned yield.

In view of these circumstances, we have tried to use an organic solvent as a diluent in place of ammonia and have found that the aforementioned effects can be obtained. Such effects are characteristic only for the cobalt catalyst. In other words, such effects cannot be obtained at all, or the yield is low, with the use of a well known hydrogenation catalyst such as nickel (Comparative Example 4), copper chromite (Comparative Example 5), platinum (Comparative Example 6), palladium (Comparative Example 7), rhodium (Comparative Example 8) or ruthenium (Comparative Example 9); only the cobalt catalyst brings about markedly superior results. By the use of the cobalt catalyst, the by-production of n-amylamine is controlled to a very low level.

Catalyst

The catalyst used in the present invention is a cobalt-based catalyst. By the term "cobalt-based catalyst" used herein are meant catalysts which owe at least the main part of their hydrogenation activity to cobalt and include those that contain a small amount of a promoter or a co-catalyst conventionally used for metal catalysts such as cobalt catalyst. An example of preferred co-catalysts is rhenium.

One embodiment of the cobalt-based catalysts preferably used in the present invention is a Raney cobalt catalyst.

The precursor alloy of the Raney cobalt is subjected to alkali leaching in an aqueous solution according to a conventional method. After the development, the catalyst is washed until no alkali ions can be detected, and then water is forced out therefrom with a solvent for the hydrogenation reaction. The catalyst is then ready for use. In the case where the solvent to be used for the hydrogenation reaction is not miscible with water, water can be first forced out with a solvent which is both soluble in water and lipophilic, and then the solvent can be forced out by the solvent to be used in the hydrogenation. The Raney's cobalt may contain co-catalyst metals such as manganese, iron, nickel, copper, molybdenum, tungsten, rhenium, and chromium. The preferred content of each metal in its ratio to cobalt is approximately 0.01 to 0.3 (atomic ratio).

The other group of the cobalt-based catalysts preferred in the present invention is reduced cobalt. The reduced cobalt is usually obtained by heating, in a stream of a reducing gas such as hydrogen, cobalt oxide which has been produced by decomposition of a cobalt salt which releases components other than cobalt comprised therein in the form of gas on the decomposition, such as basic cobalt carbonate, cobalt carbonate, cobalt hydroxide or cobalt nitrate.

The reduced cobalt can be obtained as a cobalt supported on a carrier. The cobalt supported on a carrier is produced by a process which includes a step of preparing a cobalt salt in the presence of a carrier material or a step of mixing a carrier material with a salt or oxide of cobalt and then subjecting the resulting mixture to reduction treatment. The carriers preferably used include diatomaceous earth, silica, alumina, zirconia, magnesia and the like. The carried catalysts are produced in a molded form if so desired.

The reduced cobalt may contain a co-catalyst or a promoter. A cobalt catalyst containing rhenium as the co-catalyst can be obtained by co-precipitating a rhenium compound during preparation of the above-mentioned cobalt salt, or by mixing a salt or oxide of cobalt with a rhenium compound, and then subjecting the mixture to reduction treatment. Ordinarily, it is preferable to use as a rhenium compound perrhenic acid, ammonium perrhenate, or the like. The preferred content ratio of rhenium to cobalt is approximately 0.01 to 0.3 (atomic ratio).

The reduction in the preparation of the catalyst is usually conducted in a stream of hydrogen at a temperature of 150° to 500° C., preferably at 200 to 300° C. After the reduction, the catalyst is used in an atmosphere isolated from air. It is convenient to isolate air by impregnating the catalyst with the reaction solvent because of simplicity of operation. If necessary, the reduction product is subjected to so-called stabilization treatment by gradually contacting it in an inert gas with air or carbon dioxide gas, thereby making it ready for being taken out into the air without ignition thereof.

Organic Solvent

The term "solvent" means an organic compound which is liquid under the hydrogenation conditions and dissolves the starting amine to a substantial degree.

When the amount of the solvent used is too small, the beneficial effects cannot be brought about sufficiently. On the other hand, an excessive amount of the solvent will be uneconomical and may cause inconvenient difficulties such as decrease in the reaction velocity.

A suitable amount is 0.1 to 50 times, preferably 0.5 to 30 times, the weight of the starting amine used.

The desirable effects of the solvent in the present invention are generally observed by the use of some inert organic solvents. The degree of such effects, however, varies depending on the kind of the solvent used. This fact suggests that an organic solvent does not merely act as a diluent. For example, the effects brought about by addition of cyclohexane were far superior to those obtained by the use of n-hexane, although both solvents have 6 carbon atoms (reference is made to Examples 4 and 6). Examples of the solvents which are particularly effective in the present invention are cyclic hydrocarbon compounds, oxygenated compounds and nitrogenous compounds.

Examples of the cyclic hydrocarbon compounds are monocyclic compounds of at least 5 carbon atoms such as cycloalkanes, e.g. cyclopentane, cyclohexane, cyclooctane, cyclodecane, cyclododecane, etc. and polycyclic alkanes such as decalin, and saturated anthracene.

Examples of the oxygenated compounds are tertiary alcohols (particularly saturated alcohols) and ethers, the former being illustrated by tertiary butylalcohol, 2-methyl-2-butanol and 2-methyl-2-hexanol.

The ethers are illustrated by diethylether, dipropylether, dibutylether, diamylether, and diisoamylether. The two alkyl groups in the dialkylether may be identical or different from each other, or each group may be branched. The ethers include dialkylethers of glycol, viz. dihydroxyalkane. With respect to monoglycol dialkyl ethers, the glycol moiety preferably contains 2 to 4 carbon atoms, and the alkyl groups preferably contain 1 to 5 carbon atoms (the alkyl groups having 3 or more carbon atoms may be linear or branched). As to dialkylethers of polyethyleneglycol, the alkyl groups are the same as above, and the number of the ethoxy groups linked together is 2 to 6, preferably 2 to 4. The ethers may be cyclic ethers. Dioxane and tetrahydrofuran are preferred as the solvent.

Among the nitrogenous compounds, tertiary amines (especially, saturated amines) are preferred. They include, for example, trimethylamine, and triethylamine. The alkyl groups substituted on the N atom may be identical or different from one another. A cyclic imine having an alkyl group on the N atom such as N-pentyl piperidine is a preferred solvent. An ether bond may be present in the ring, which is illustrated by an N-alkyl morpholine.

Conditions for Hydrogenation Reaction

The conditions for the hydrogenation reaction except the kinds of the catalyst and the solvent used may be optionally selected as long as they result in the objective liquid-phase hydrogenation reaction.

The reaction temperature is of the order of 100° to 400° C., preferably of the order of 150° to 300° C.

The reaction pressure is of the order of 5 to 200 atm., preferably of the order of 10 to 150 atm.

The amount of the catalyst used is suitably 0.001 to 0.5, preferably 0.01 to 0.3 time the weight of the starting amine used.

The reaction can be conducted either continuously or in a batchwise operation.

The starting amine may be either one of furfurylamine and tetrahydrofurfurylamine or a mixture thereof.

EXPERIMENTAL EXAMPLES

EXAMPLE 1

To 25 g of 25% NaOH aqueous solution was added gradually 4 g of a Raney cobalt alloy (Co:Al=1:1) with stirring at room temperature so that no remarkable exothermic heat was observable. The resulting mixture was heated to 50° C. After one hour, decantation was carried out.

Then the resulting material was washed with 100 ml of warm water 8 times with decantation. The resulting Raney cobalt catalyst was washed 8 times with 100 ml of dioxane.

Into a 50 cc autoclave equipped with stirrer were charged 0.2 g of this Raney cobalt catalyst, 18.2 g of dioxane as a solvent, and 2.0 g of tetrahydrofurfurylamine. Hydrogen was introduced thereinto, and reaction was conducted for one hour at a reaction temperature of 210° C., under a reaction pressure of 60 kg/cm$^2$, and at a stirring velocity of 1,000 rpm. After the autoclave was cooled, the reaction product was filtered off from the catalyst and was analyzed by gas chromatography. The results are shown in Table 1.

EXAMPLES 2 AND 3

Experiments were carried out by repeating the treatment and reaction under the conditions of Example 1 except that a Raney cobalt-manganese alloy (Co:Mn:Al=30:3.5:66.5) [Example 2] and a Raney cobalt-iron alloy (Co:Fe:Al=47.6:2.4:50) [Example 3] were used. The results as shown in Table 1 were obtained.

EXAMPLE 4

To an aqueous solution of 150 g of cobalt nitrate (Co(NO$_3$)$_2$.6H$_2$O) dissolved in 175 ml of distilled water was added dropwise with stirring over 2 hours an aqueous solution of 141 g of ammonium bicarbonate (NH$_4$HCO$_3$) dissolved in 650 ml of distilled water, while the system was maintained at 20° to 22° C. The resulting precipitate of basic cobalt carbonate was filtered and amply washed with distilled water to obtain a cake of basic cobalt carbonate salt (Co content: 9.09% by weight). After drying at 100° to 110° C. for 12 hours, the cake was pulverized. The powder thus obtained was treated in a stream of air for 1 hour at 450° C., which step was followed by reduction treatment in a stream of hydrogen at 300° C. for 2 hours. The resulting cobalt catalyst was dispersed in a solvent to be used in the subsequent reaction, thus air being isolated therefrom for storage of the catalyst.

The catalyst thus obtained was used for the reaction under the same conditions as in Example 1 by using tetrahydrofurfurylamine as the raw material. The results as shown in Table 1 were obtained.

EXAMPLE 5

By repeating the procedure in Example 4 except that 1.96 g of ammonium perrhenate (NH$_4$ReO$_3$) in the form of an aqueous solution was added to 165 g of a cake of basic cobalt carbonate salt (containing 15 g of Co), and the resulting mixture was amply kneaded, which step was followed by kneading and drying under heating to about 80° C., whereupon a cobalt-rhenium catalyst (Re/Co=0.03 in atomic ratio) was obtained. The catalyst thus obtained was used in the reaction under the conditions in Example 1 except that the reaction time was 15 minutes, whereupon the results shown in Table 1 were obtained.

EXAMPLES 6 THROUGH 11

The reaction under the conditions of Example 1 was repeated except that as the solvent n-hexane (Example 6), 2,2,4-trimethylpentane (Example 7), cyclohexane (Example 8), decalin (Example 9), diisopropylether (Example 10), and N-methylmorpholine (Example 11) were respectively used. The results obtained were as shown in Table 2.

EXAMPLES 12 THROUGH 16

A reaction under the conditions of Example 5 was repeated except that as the solvent tertiarybutylalcohol (Example 12), ethyleneglycoldimethylether (Monoglyme) (Example 13), diethyleneglycoldimethylether (Diglyme) (Example 14), triethylamine (Example 15), and N-pentylpiperidine (Example 16) were respectively used. The results as shown in Table 2 were obtained.

EXAMPLE 17

A reaction was conducted under the conditions of Example 4 except that furfurylamine was used as the raw material. The results are shown in Table 3.

EXAMPLE 18

A reaction was conducted under the conditions of Example 17 except that the reaction was carried out at a reaction temperature of 120° C. under a reaction pressure of 50 kg/cm$^2$ for 200 minutes and then at 210° C. and 60 kg/cm$^2$ for another 60 minutes. The results are shown in Table 3.

COMPARATIVE EXAMPLE 1

A reaction was conducted under the conditions set forth in Example 4 of U.S. Pat. No. 2,265,201 except that a 50 cc autoclave equipped with a stirrer was charged with 1.0 g of the Raney cobalt catalyst as described in Example 1 and 10.0 g of furfurylamine. Then 4.0 g of liquid ammonia was added thereto at 0° C. with stirring, a reaction pressure of 135 kg/cm$^2$ being used. The autoclave was cooled, and the reaction product was filtered off from the catalyst and analyzed by gas chromatography. The results are shown in Table 2.

COMPARATIVE EXAMPLE 2

The procedure of Comparative Example 1 was repeated except that a 50 cc autoclave equipped with a stirrer was charged with 0.2 g of the Raney cobalt catalyst, 18.2 g of methanol as a solvent, and 2.0 g of tetrahydrofurfurylamine, and then 0.8 g of liquid ammonia was added thereto at 0° C. with stirring. The results are shown in Table 2.

COMPARATIVE EXAMPLE 3

A reaction was conducted under the conditions of Example 1 except that no solvent was used and that the catalyst and tetrahydrofurfurylamine was used in the amounts of 1.5 g and 15.2 g, respectively. The results are shown in Table 2.

COMPARATIVE EXAMPLES 4 THROUGH 9

Reactions were conducted under the conditions in Example 1 except that as a catalyst 0.2 g each of a commercially available stabilized nickel (Comparative Example 4), copper chromite (Comparative Example 5), platinum (5% by weight) on activated carbon (Comparative Example 6), palladium (5% by weight) on activated carbon (Comparative Example 7), rhodium (5% by weight) on activated carbon (Comparative Example 8) and ruthenium (5% by weight) on activated carbon (Comparative Example 9) were respectively used. The results are shown in Table 2.

TABLE 1

Comparison of catalysts

| | | Catalyst | Conversion of starting amine (mol %) | Yield of piperidine (%) |
|---|---|---|---|---|
| Examples | 1 | Raney Co | 96.4 | 82 |
| | 2 | Raney Co—Mn | 98.9 | 87 |
| | 3 | Raney Co—Fe | 99.3 | 86 |
| | 4 | Reduced Co | 98.0 | 83 |
| | 5 | Reduced Co—Re | 98.9 | 84 |
| Comparative Examples | 4 | Stabilized Ni | 64.8 | 2.7 |
| | 5 | Cu—Cr$_2$O$_3$ | 0 | 0 |
| | 6 | Pt | 0 | 0 |
| | 7 | Pd | 30.5 | 0 |
| | 8 | Rh | 38.9 | 0 |
| | 9 | Ru | 60.0 | 6.7 |

TABLE 2

Effects of solvent

| | | Solvent | Conversion of starting amine (mol %) | Yield of piperidine (%) |
|---|---|---|---|---|
| Examples | 6 | n-hexane | 89.0 | 62 |
| | 7 | 2,2,4-trimethylpentane | 97.7 | 75 |
| | 8 | cyclohexane | 99.7 | 81 |
| | 9 | decalin | 97.4 | 75 |
| | 10 | diisopropylether | 97.8 | 81 |
| | 11 | N—methylmorpholine | 94.9 | 81 |
| | 12 | tert.-butylalcohol | 96.7 | 62 |
| | 13 | ethyleneglycol dimethylether | 96.5 | 70 |
| | 14 | diethyleneglycol dimethylether | 84.0 | 56 |
| | 15 | triethylamine | 94.4 | 80 |
| | 16 | N—pentylpiperidine | 95.7 | 75 |
| Comparative Examples | 1 | no solvent* | 99.9 | 22 |
| | 2 | methanol* | 43.0 | 1.4 |
| | 3 | no solvent | 92.6 | 46 |

*U.S. Pat. No. 2,265,201

TABLE 3

| Examples | Conversion of starting material (mol %) | Yield of piperidine (%) |
|---|---|---|
| 17 | 100 | 79 |
| 18 | 100 | 84 |

What is claimed is:

1. A process for producing piperidine by catalytic hydrogenation in a liquid-phase of a starting amine selected from the group consisting of furfurylamine, tetrahydrofurfurylamine and mixtures thereof, characterized in that the catalyst used is a cobalt-based catalyst and in that the starting amine is in a state of dilution with an organic solvent.
2. The process according to claim 1, wherein the catalyst is a Raney cobalt catalyst.
3. The process according to claim 2, wherein the Raney cobalt catalyst contains as a promoter at least one metal selected from the group consisting of manganese, iron, nickel, copper, molybdenum, tungsten, rhenium and chromium.
4. The process according to claim 1, wherein the catalyst is reduced cobalt.
5. The process according to claim 4, wherein the reduced cobalt contains rhenium as a co-catalyst.
6. The process according to claim 1, wherein the solvent is a cyclic hydrocarbon which is liquid under the hydrogenation conditions.
7. The process according to claim 6, wherein the cyclic hydrocarbon is a monocyclic alkane having at least 5 carbon atoms.
8. The process according to claim 6, wherein the cyclic hydrocarbon is a polycyclic compound selected from the group consisting of decalin and saturated anthracene.
9. The process according to claim 1, wherein the solvent is an oxygenated compound selected from the group consisting of tertiary alcohols and ethers which are liquid under the hydrogenation conditions.
10. The process according to claim 1, wherein the solvent is a tertiary amine which is liquid under the hydrogenation conditions.
11. The process according to claim 1, wherein the starting amine is furfurylamine.
12. The process according to claim 1, wherein the hydrogenation is conducted in the substantial absence of added ammonia.

* * * * *